United States Patent [19]
Gaddie, Sr.

[11] 3,961,603
[45] June 8, 1976

[54] HABITAT FOR EARTHWORM CULTIVATION

[76] Inventor: Ronald E. Gaddie, Sr., 1140 W. Philadelphia, Ontario, Calif. 91761

[22] Filed: July 31, 1975

[21] Appl. No.: 600,570

[52] U.S. Cl. .................................. 119/15; 220/380
[51] Int. Cl.² ........................................ A01K 67/00
[58] Field of Search ..................... 119/15, 1, 16, 19; 220/380

[56] References Cited
UNITED STATES PATENTS

| | | | |
|---|---|---|---|
| 3,129,692 | 4/1964 | Sanderson............................ | 119/15 |
| 3,654,903 | 4/1972 | Montgomery......................... | 119/15 |

*Primary Examiner*—Russell R. Kinsey
*Assistant Examiner*—J. N. Eskovitz
*Attorney, Agent, or Firm*—Boniard I. Brown

[57] ABSTRACT

A small-scale habitat for the cultivation of earthworms is designed for the optimum production of live worms, eggs and worm castings. The habitat comprises a plurality of superimposed, stackable containers with perforated bottoms and inward projections at their upper flanges. These projections sustain the weight of the upper containers, admit air to each individual container and permit feeding and breeding activity by earthworms at all levels of the stacked assembly; the movement of the earthworms from one level to another being facilitated by the aforementioned perforations in the bottoms of the containers. The bottommost container has an unperforated bottom and is adapted to hold water in a matrix of pebbles or crushed stone for the control of the moisture content of bedding, suitably peat-moss or coarse earth, in the superior containers.

6 Claims, 4 Drawing Figures

U.S. Patent June 8, 1976 3,961,603
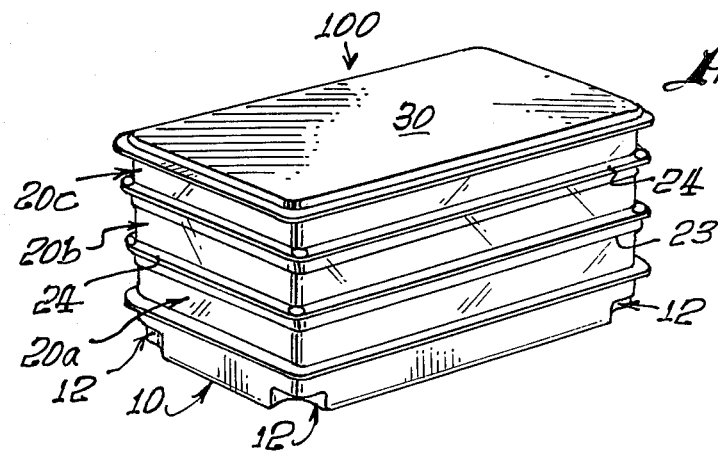
Fig. 1.
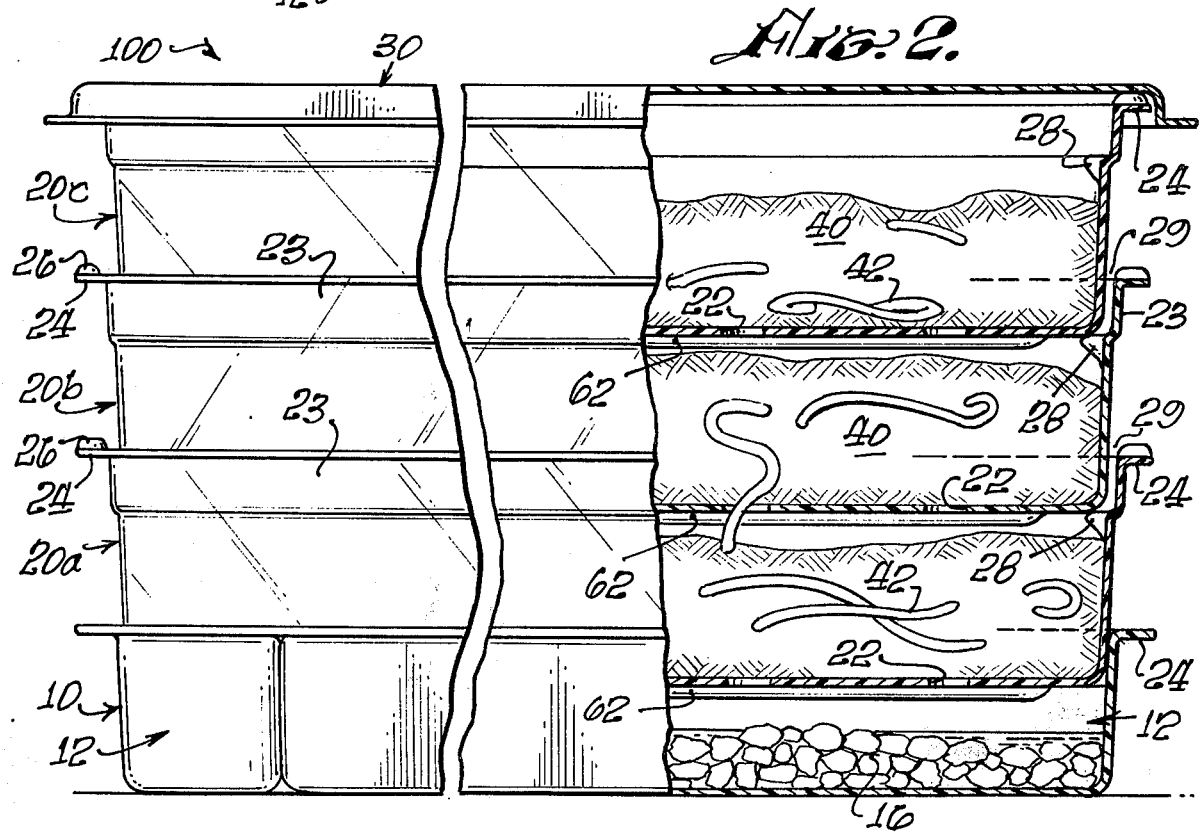
Fig. 2.
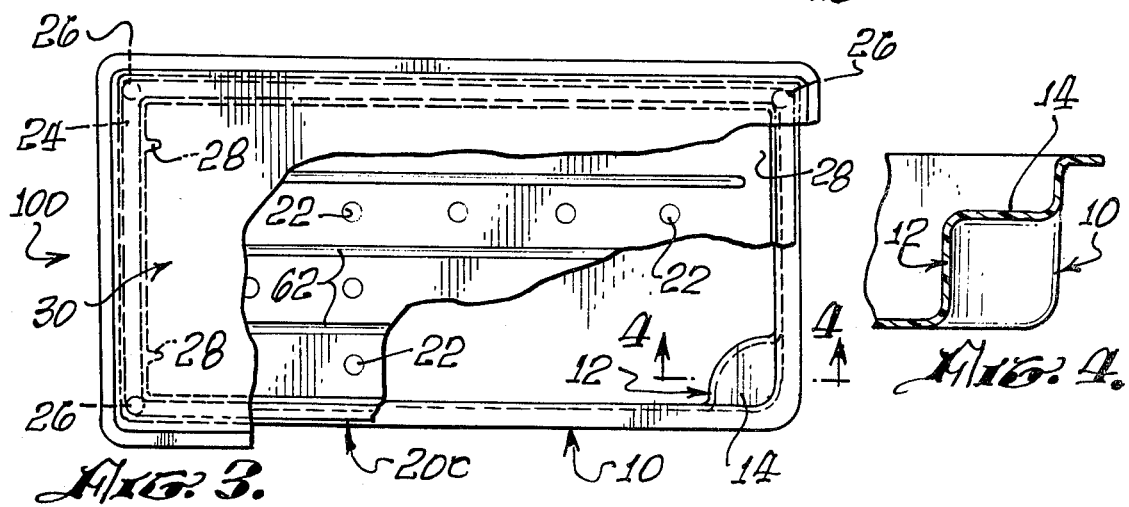
Fig. 3.
Fig. 4.

HABITAT FOR EARTHWORM CULTIVATION

BACKGROUND OF THE INVENTION

This invention relates to a habitat for the controlled farming of earthworms. It relates, more particularly, to such a habitat which is optimally adapted to all phases of commercial earthworm farming, including the production of live worms, of worm eggs as reproductive stock, and of worm castings for fertilizer.

The farming of earthworms has developed over the years into an integrated economic activity. The initial demand was for earthworms for fishing bait and required little sophistication, being based essentially on the removal of worms from garden soil or from partially buried breeding chambers, such as the one taught by Lebiedzinski in U.S. Pat. No. 2,867,055.

With the growing popularity of organic farming a demand developed for the manure produced by earthworms which is particularly rich in nutrients for plant life. The prior art teaches method and apparatus for leaching the excrement from earth containing worms, such as taught by Montgomery in U.S. Pat. No. 3,654,903.

Additional income may be derived from farming earthworms for the production of breeding stock in the form of dried eggs.

It is, therefore, a primary object of the invention to provide a farming structure for earthworms adapted to the efficient and simultaneous production of live worms, eggs and castings.

It is a further object of the invention to provide such a structure, or habitat, which is simple in construction and economical in use.

It is an additional object of the invention to provide a habitat for earthworm farming wherein the prevailing conditions of temperature, humidity and food distribution are automatically maintained at an optimum level.

Other objects and advantages of the invention shall become apparent from the detailed description of the preferred embodiment thereof, below.

SUMMARY OF THE INVENTION

The objects of the invention are attained in a farming structure comprised of a plurality of shallow pans constructed from an impermeable material, suitably a thermoset plastic, and provided with peripheral flanges with convex buttons projecting upwardly from said flanges and with inwardly projecting gussets just below the plane of the flanges.

It is the function of the gussets to bear the weight of superimposed pans, the farming structure being a stacked assembly of such pans, while the convex buttons of the uppermost pan are adapted to secure a planar lid just above the flange surface.

The individual pans are so shaped that the periphery of the base portions thereof is slightly smaller than the periphery of the upper, flanged portions, so that the stacked assembly provides for narrow ventilating slits between each of the superposed pans and the topmost pan and the lid. These slits are so sized that earthworms cannot penetrate through them and are restrained to remain within the habitat stack.

Each pan bears a plurality of perforations in each bottom, with the exception of the bottom-most pan, large enough in dimension to permit the ready movement of worms from one level in the stack to another.

The bottom-most pan is advantageously constructed in a slightly different shape from those above. The perforations in its bottom are omitted since the primary function of the base pan is to retain water in a liquid form and to control the humidity within the habitat by evaporation and/or condensation. For this purpose the bottom pan is charged with pebbles, or crushed stone, to provide a substantial mass of thermal inertia and a large surface area for the mass exchange of water with the surroundings.

The upper portion of the bottom pan is also advantageously formed in such a manner that it engages the base of the next pan in the stacked assembly in a sealing relationship.

The pans wherein the farming of earthworms is conducted, excepting the bottom-most pan of the stack, are charged with a medium, most suitably peat moss, which provides for ease of travel of the earthworms, for good ventilation, and for the retention of eggs and castings. The quantity of moss is controlled in each pan so that the bedding material just fills each pan to the level defined by the upper surfaces of the gussets projecting inwardly in the upper regions thereof. This ensures that the bedding material is continuous throughout the stack, without excessive airgaps between successive pans and without undue compression of the bedding material in any of the subordinate pans.

The method of farming earthworms in the habitat of the invention begins with colonizing the bedding material therein with earthworms of the desired type, such as red worms, charging water into the base container for the control of humidity, and adding some suitable food to the surface of the uppermost container, prior to placing the cover thereon.

The worms will readily distribute themselves over the several levels of the habitat, travelling toward the surface for feeding and breeding and into the lower levels for the deposition of eggs.

Nutrients are periodically added to the topmost pan. Water is periodically added to the top container, and excess water flows downwardly to the bottom tray where it is depleted by evaporation.

At suitable intervals the uppermost pan is removed and the worms, eggs and manure separated from the bedding material. The pan is then recharged with peat moss, or other suitable bedding, and replaced in the stack as the penultimate pan towards the base. In this manner each pan migrates from the bottom of the stack towards the top and, thereafter, returns to a start position next to the humidity controlling bottom pan.

It has been found in practice that a single habitat with three farming pans, each with typical dimensions of the order of 9 inches by 18 inches by 2 inches, can produce $75 in castings—manure— and approximately $300 in live worms and eggs, each year.

BRIEF DESCRIPTION OF THE DRAWINGS

FIG. 1 is a perspective view of a worm habitat of the invention, including a humidity control pan, three breeding pans, and a cover;

FIG. 2 is a frontal elevation of the habitat of FIG. 1, in partial section, illustrating the interrelationship of the several parts thereof;

FIG. 3 is a plan view of the same assembly, in partial sections showing several levels thereof; and FIG. 4 is a partial, sectioned, view of one corner of the bottom pan, taken along section line 4—4 of FIG. 3.

DESCRIPTION OF THE PREFERRED EMBODIMENT

The perspective view of FIG. 1 shows an earthworm habitat 100 of the invention including a base pan 10, breeding pans 20a, 20b and 20c, and a cover 30.

A frontal view of the habitat 100, in partial section, is also shown in FIG. 2 with the pans 20 charged with bedding 40 in which earthworms 42 gambol.

The corners of the bottom pan 10 are deformed inwardly to form support structures 12 on whose upper surfaces 14 the bottom of pan 20a rests. The sidewalls of pan 10, as well as those of the pans 20, are formed with a slight, upwardly opening draft, so that the base of one fits into the top of another in setting up the stacked structure of the habitat 100. The dimensions are so selected that, when a pan 20 is slipped into the top of pan 10, the walls form a reasonably tight seal against each other as the pan 20a rests upon the flats 14.

By this means the internal volume of the base pan 10 is sealed off from the atmosphere and connected to the volume of pan 20a through orifices 22, a plurality of which is provided in the basal plane of each of the pans 20.

A layer of gravel 16, or other water-impermeable filler of great surface area, is charged into the pan 10 which is then partially filled with water. Since the internal volume of the pan 10 is sealed from the atmosphere outside the habitat 100, but is in communication with the internal volumes therein, via the orifices 22, the liquid reservoir inside the bottom pan will automatically attempt to maintain the relative humidity inside the habitat at a high level, approaching 100%, by evaporation from the exposed surfaces of the gravel bed 16.

This evaporative, humidity control is superior to the methods of the prior art which required the direct descanting of water over the earth in which the earthworms moved, resulting in waterlogging on one hand, and in the leaching of the worm castings into a dilute fertilizer solution.

A typical pan 20 is constructed with an upper rim 23 which is outwardly spaced by a small amount from the sidewall 21 of the pan. The offset of the rim 21 serves, in conjunction with gussets, or support tabs, 28 to define a ventillating gap 29 between two stacked pans. The gap 29 is very small in dimension and does not permit even a small earthworm from ascending through it, but does assist in aerating the bedding 40 in the habitat 100. The gussets 28 are small, inwardly projecting tabs which the base of the ulterior pan and prevent it from resting on the peat moss in the pan below. The rim 23 terminates in an outwardly turned, substantially horizontal flange 24, the upper surface of which bears at intervals, suitably at the four corners of the pan, convex buttons 26. The buttons 26 are operative in only the uppermost pan 20 of a stack and support the cover 30 in a spaced relationship with respect to the uppermost pan 20c.

Since the pans 20 are sequentially rotated in normal use, each of them will at some time occupy the uppermost position in the stack and buttons 26 are, therefore, molded into, or cemented onto, all flanges 24.

The pans 20 are, by preference, constructed from a clear plastic material to admit daylight. A certain amount of light, such as is normally available in a room is conducive to good health and growth in the habitat; where necessary, artificial light may also be provided, but care must be taken to keep the water level in pan 10 at the desired elevation, to supply the increased evaporation attendant on excess heat of lamps.

No buttons 26 are provided in the flange of base pan 10, since this particular pan is not called upon to support the cover at any time in the earthworm-raising cycle.

The plan view of FIG. 3 indicates some constructional details of the habitat assembly, emphasized by partial sections at several elevations through the stack. The orifices 22 are clearly visible in the base of a typical pan 20, as are ribs 62 which serve as structural reinforcements therein.

The partial section of FIG. 4 illustrates the construction of the support plane 14 in the lower corners of the pan 10, atop an inward deformation of corner portion 12.

The preferred embodiment of the earthworm habitat of the invention, as described hereinabove with reference to the preferred embodiment 100 thereof, provides a simple and economical structure for the raising of earthworms and for the recovery of earthworm castings for fertilizer and of eggs for propagation.

The measures of humidity, aeration and earthworm movement between the several levels of the habitat are controlled by means of integral structural elements; minor changes in the size, shape and arrangement of these elements are possible and are deemed encompassed by the invention, delimited only by the appended claims.

The inventor claims:

1. A habitat for the raising of earthworms in a bedding matrix, comprising:
    a plurality of stacked pans, each of said pans being provided with a flat bottom; perforations in that bottom, for the circulation of air, moisture and earthworms therethrough; peripheral sidewalls with an upwardly opening draft, defining spaces for the charging thereinto of said bedding; gusset means, projecting inwardly from said sidewalls into said spaces, for the support of a superior pan thereon; and with upwardly convex spacing buttons, in a substantially horizontal flange extending around the upper circumference of said sidewalls;
    a humidity control pan with a water-impermeable base and peripheral walls, adapted to sealably receive the lowermost one of said plurality of stacked pans; and
    a cover, overlapping the circumferential flange of the topmost one of said plurality of stacked pans, supported on the spacing buttons thereon.

2. The habitat of claim 1, wherein:
    said humidity control pan further comprises support plane means, for bearing the weight of said plurality of stacked pans, of the bedding charged thereinto, and the weight of said cover.

3. The habitat of claim 1, wherein:
    the number of said plurality of stacked pans is three.

4. The habitat of claim 1, wherein:
    said habitat is constructed from a thermosetting plastic composition.

5. A method of raising earthworms in a habitat comprised of a plurality of breeding pans charged with bedding and stacked in a vertical array, with a humidity control pan underneath the lowermost breeding pan and chargeable with water, and with a cover superimposed on the topmost breeding pan, comprising the steps of:

introducing earthworms into said topmost breeding pan;

charging water into said humidity control pan;

periodically removing the contents from said topmost pan;

separating live worms, worm eggs and worm castings from said removed contents;

replacing said bedding into the topmost pan; and exchanging said topmost pan for the pan proximate to said humidity control pan.

6. The method of claim 5, further comprising the steps of:

periodically replenishing said nutrients in said topmost of said breeding pans; and periodically recharging said humidity control pan with water.

* * * * *